United States Patent
Fujii et al.

(10) Patent No.: US 10,701,790 B2
(45) Date of Patent: Jun. 30, 2020

(54) X-RAY IMAGING APPARATUS

(71) Applicant: SHIMADZU CORPORATION, Nakagyo-ku, Kyoto-shi, Kyoto (JP)

(72) Inventors: Hideki Fujii, Kyoto (JP); Tomoharu Okuno, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 231 days.

(21) Appl. No.: 15/647,827

(22) Filed: Jul. 12, 2017

(65) Prior Publication Data
US 2019/0021157 A1    Jan. 17, 2019

(51) Int. Cl.
| | | |
|---|---|---|
| H05G 1/26 | (2006.01) | |
| H05G 1/28 | (2006.01) | |
| H05G 1/46 | (2006.01) | |
| H05G 1/56 | (2006.01) | |
| H05G 1/36 | (2006.01) | |
| H05G 1/58 | (2006.01) | |

(Continued)

(52) U.S. Cl.
CPC .............. *H05G 1/26* (2013.01); *A61B 6/545* (2013.01); *H05G 1/28* (2013.01); *H05G 1/36* (2013.01); *H05G 1/44* (2013.01); *H05G 1/46* (2013.01); *H05G 1/58* (2013.01); *A61B 6/566* (2013.01); *H05G 1/56* (2013.01)

(58) Field of Classification Search
CPC .. H05G 1/26; H05G 1/28; H05G 1/36; H05G 1/56; A61B 6/545; A61B 6/566
See application file for complete search history.

(56) References Cited

U.S. PATENT DOCUMENTS

| | | | | |
|---|---|---|---|---|
| 2002/0080918 A1* | 6/2002 | Sako | ........................ | A61B 6/00 378/115 |
| 2004/0071263 A1* | 4/2004 | Motoki | .................. | G16H 40/63 378/98 |
| 2013/0259196 A1* | 10/2013 | Tajima | ..................... | A61B 6/42 378/62 |

FOREIGN PATENT DOCUMENTS

| | | |
|---|---|---|
| JP | 2000-350718 | 12/2000 |
| JP | 2003-10160 | 1/2003 |
| JP | 2003-302716 | 10/2003 |

(Continued)

OTHER PUBLICATIONS

JP Pat. Appln. No. 2015-011084, Notification of Reasons for Refusal dated Apr. 2, 2018, 3 pages—English, 3 pages—Japanese.

*Primary Examiner* — Christine S. Kim
(74) *Attorney, Agent, or Firm* — Andrew F. Young, Esq.; Lackenbach Siegel, LLP

(57) ABSTRACT

An X-ray imaging apparatus operates by selecting an appropriate exposure sensitivity corresponding to the X-ray detector to be used. In the apparatus, an exposure sensitivity corresponding to the flat panel detectors used for an X-ray imaging is selected from multiple exposure sensitivities stored in an exposure sensitivity memory unit of the console, and the selected exposure sensitivity is displayed on the display unit of the high-voltage unit. An exposure control is executed based on the exposure sensitivity corresponding to the flat panel detectors used for the X-ray imaging, which is selected from multiple exposure sensitivities stored in an exposure sensitivity memory unit. The exposure control unit of the high-voltage unit suspends the X-ray irradiation from the X-ray tube when an integrated value of the X-ray detected by the X-ray dose sensor reaches to the setting-value set relative to the selected exposure sensitivity.

3 Claims, 5 Drawing Sheets

(51) Int. Cl.
*H05G 1/44* (2006.01)
*A61B 6/00* (2006.01)

(56) References Cited

FOREIGN PATENT DOCUMENTS

| | | |
|---|---|---|
| JP | 2008-220724 | 9/2008 |
| JP | 2013-70866 | 4/2013 |

\* cited by examiner

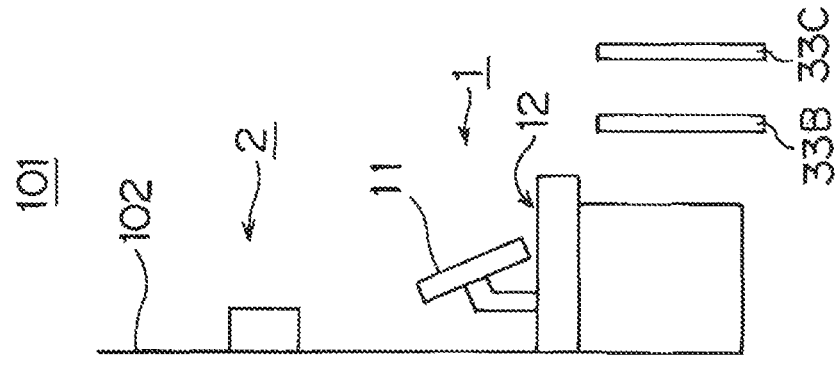
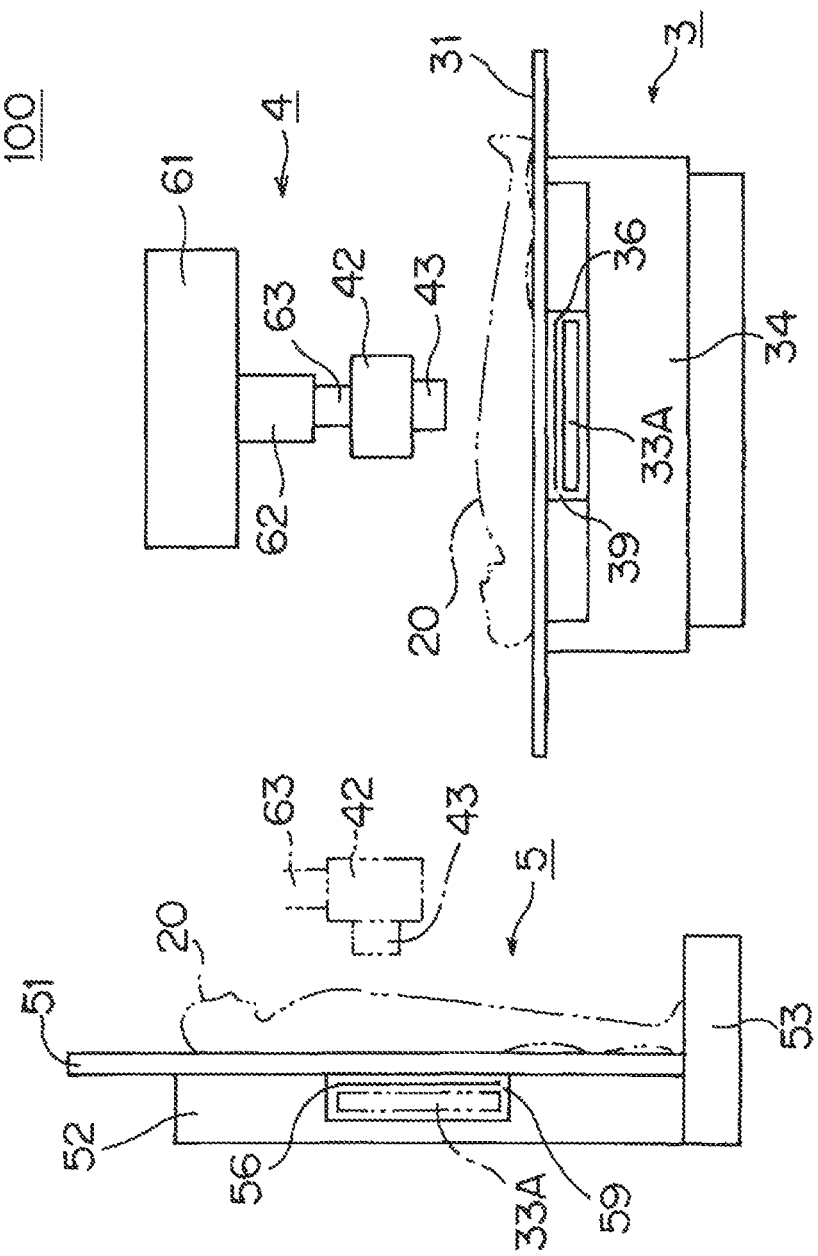

X-RAY IMAGING APPARATUS

CROSS REFERENCE TO RELATED APPLICATIONS

This application relates to, but does not claim priority from, JP 2015-011084 Filed Jan. 23, 2016, the entire contents of which are incorporated herein by reference.

FIGURE SELECTED FOR PUBLICATION

FIG. 2

BACKGROUND OF THE INVENTION

Field of the Invention

The present invention relates to an X-ray imaging apparatus (system) comprising an X-ray tube and a detector that detects the X-ray which is irradiated from the X-ray tube and transmitted through the irradiated subject.

Description of the Related Art

Such X-ray imaging apparatus use a system called AEC (Automatic Exposure Control). Such AEC systems include an X-ray dose sensor that detects the X-ray dose irradiated from the X-ray tube to the subject, and an exposure control unit that suspends the X-ray irradiation based on the integrated value of the X-ray dose detected by the X-ray dose sensor; and suspends the X-ray imaging when the predetermined X-ray dose for the subject is irradiated to the subject (Patent Document 1).

RELATED PRIOR ART DOCUMENTS

Patent Document

Patent Document 1: JP Patent Published 2003-10160

ASPECTS AND SUMMARY OF THE INVENTION

According to one aspect of the present invention there is provide an X-ray imaging apparatus operates by selecting an appropriate exposure sensitivity corresponding to the X-ray detector to be used. In the apparatus, an exposure sensitivity corresponding to the flat panel detectors used for an X-ray imaging is selected from multiple exposure sensitivities stored in an exposure sensitivity memory unit of the console, and the selected exposure sensitivity is displayed on the display unit of the high-voltage unit. An exposure control is executed based on the exposure sensitivity corresponding to the flat panel detectors used for the X-ray imaging, which is selected from multiple exposure sensitivities stored in an exposure sensitivity memory unit. The exposure control unit of the high-voltage unit suspends the X-ray irradiation from the X-ray tube when an integrated value of the X-ray detected by the X-ray dose sensor reaches to the setting-value set relative to the selected exposure sensitivity.

According to an X-ray imaging apparatus including such AEC, the X-ray imaging apparatus sets up the exposure sensitivity of the AEC corresponding to the sensitivity of the intensifying screen to the X-ray when an X-ray image is taken by using the intensifying screen mounted in a cassette. Specifically, multiple kinds of the intensifying screen are available corresponding to an imaging region and purposes, and an operator understanding the sensitivity of the intensifying screen executes the X-ray imaging switching the exposure sensitivity of the AEC.

On the other hand, recently, an X-ray detector such as a flat panel detector and so forth is being used, instead of such intensifying screen. Relative to the X-ray detector, multiple kinds of such detectors are being selectively used depending on the imaging region and the purpose therefor. In such case, the operator may not consider the difference of sensitivity between the detectors in many applications, differently from the case using the intensifying screen. Therefore, it is problematic that the radiation exposure dose to the subject is much higher than the requirement dose for the subject because the setting of the exposure sensitivity of the AEC might not match to the sensitivity of the X-ray detector, or the X-ray dose might not satisfy the requirement dose for the imaging.

In addition, it is feasible that a plurality of imaging conditions depending on the imaging regions and applications can be stored in advance, but if all conditions relative to the AEC exposure sensitivity corresponding to the sensitivity of each X-ray detector as well as a variety of imaging conditions are stored, the number of imaging conditions can be extremely high, and consequently, it is problematic that not only even a selection per se of the imaging condition is difficult, but also extra memories to store many data can be required.

The present invention is completed to solve the above problems and the purpose thereof is to provide an X-ray imaging apparatus that is feasible in performing an adequate X-ray imaging by selecting an appropriate exposure sensitivity corresponding to the X-ray detector to be used.

Means for Solving the Problem

According one alternative aspect of the present invention, there is provided an X-ray imaging apparatus comprising: an X-ray tube; an X-ray detector that detects the X-ray which is irradiated from the X-ray tube to a subject and transmits through the subject; an X-ray dose sensor that detects an X-ray dose irradiated from the X-ray tube to the subject; an exposure control unit that suspends the X-ray irradiation from the X-ray tube based on an integrated value of the X-ray dose detected by the X-ray dose sensor; and further comprising: an exposure sensitivity memory unit that stores multiple exposure sensitivities indicating a relationship between the integrated values of the X-ray detected by the X-ray dose sensor and the time when the X-ray irradiation from the X-ray tube is subject to suspension corresponding to the type and class of the X-ray detector; and an identification unit that identifies the X-ray detector used for the X-ray imaging; wherein the exposure control unit selects one of multiple exposure sensitivities stored in the exposure sensitivity memory unit based on the class and type of the X-ray detector identified by the identification unit, and suspends the X-ray irradiation from the X-ray tube based on the selected exposure sensitivity.

According to another alternative aspect of the present invention, there is provided an X-ray imaging apparatus further comprising: a holding unit that attachably and detachably holds multiple kinds of the X-ray detectors; wherein the identification unit identifies a type and class of the X-ray detector held by the holding unit.

According to another alternative aspect of the present invention, there is provided an X-ray imaging apparatus further comprising: multiple holding units that hold the X-ray detectors; and an operation method selection unit that selects the holding unit; wherein the identification unit identifies the type and class of the X-ray detector held by the holding unit selected by the operation method selection unit.

According to another alternative aspect of the present invention, there is provided an X-ray imaging apparatus further comprising: a display unit that displays the exposure sensitivity selected by the exposure control unit.

Effect of the Invention

According to aspects of the present invention, there is an X-ray imaging apparatus that operably selects one of multiple exposure sensitivities based on the X-ray detector used to perform an X-ray imaging and suspends the X-ray irradiation from the X-ray tube based on the selected exposure sensitivity, so that an appropriate exposure sensitivity corresponding to the X-ray detector to be used can be selected and an adequate X-ray imaging can be implemented.

According to another aspect of the present invention, there is an X-ray imaging apparatus that operably enables an operator to be aware of the relationship between the selected X-ray detector and the exposure sensitivity needed therefor.

The above and other aspects, features and advantages of the present invention will become apparent from the following description read in conjunction with the accompanying drawings, in which like reference numerals designate the same elements.

BRIEF DESCRIPTION OF THE DRAWINGS

FIGS. 1A, 1B, 1C are schematic views of an X-ray imaging apparatus according to an aspect of the present invention.

DETAILED DESCRIPTION OF THE PREFERRED EMBODIMENTS

Figure 2:
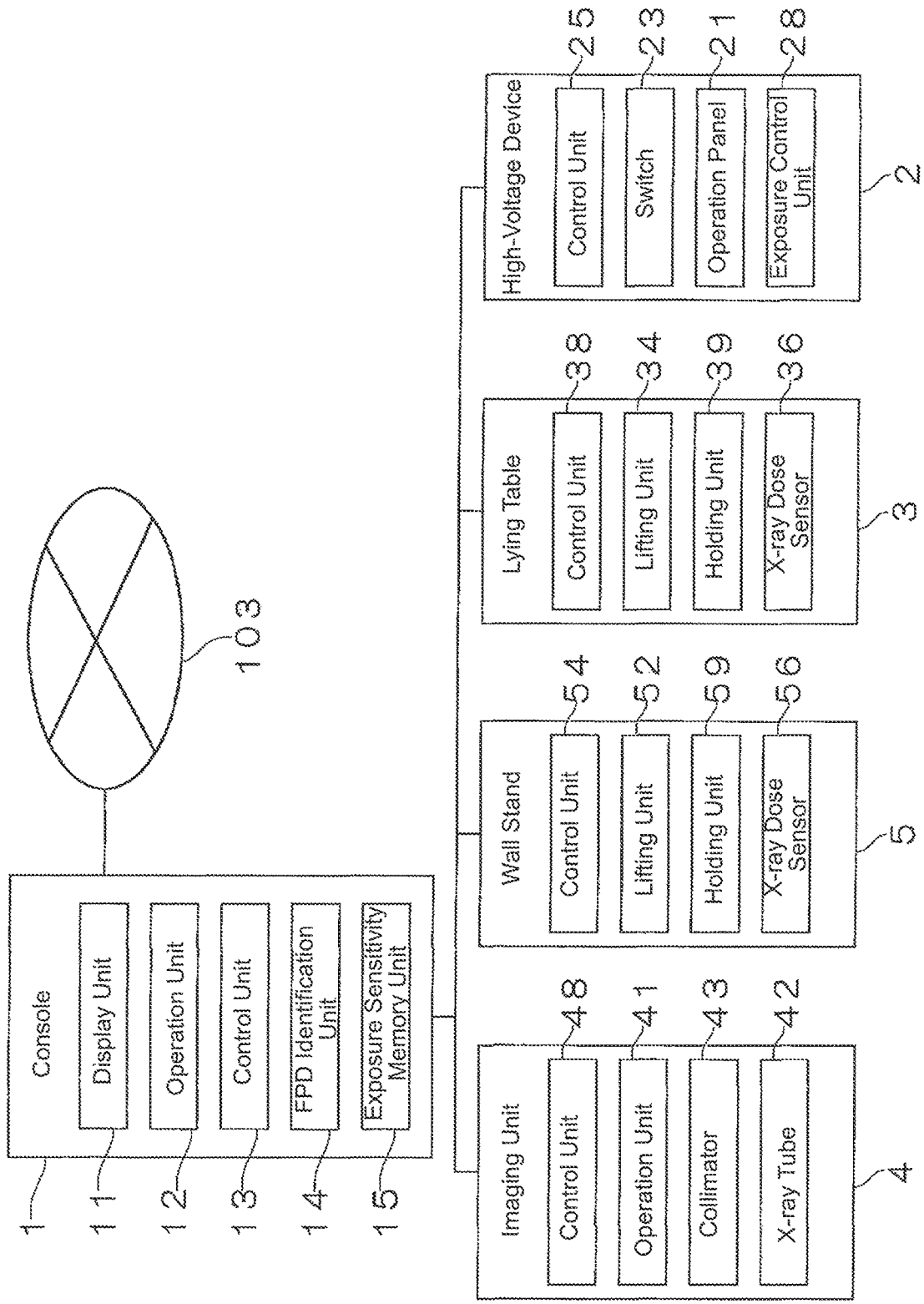
FIG. 2 is a block diagram illustrating the main control system of the X-ray imaging apparatus according to an aspect of the present invention.

Reference will now be made in detail to embodiments of the invention. Wherever possible, same or similar reference numerals are used in the drawings and the description to refer to the same or like parts or steps. The drawings are in simplified form and are not to precise scale. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

As used herein, a a computer related-type system includes an input device for receiving data, an output device for outputting data in a form (e.g. signal output, data output, printing or displaying on a computer screen), a memory for storing data as well as computer code, and a microprocessor for executing computer code wherein said computer code resident in said memory and will physically cause a processor to determine a next-step based upon any stored coding therein.

It will be further understood by those of skill in the art that the apparatus and devices and the elements herein, without limitation, and including any sub components such as operational structures, one or more circuits, communication pathways, emitters, sensors, and related elements, control and input and output structures of all kinds, display circuits and display systems and elements, any necessary driving elements, inputs, sensors, detectors, memory elements, processors and any combinations of these structures etc. as will be understood by those of skill in the art as also being identified as or capable of operating the systems and devices and subcomponents noted herein and structures that accomplish the functions without restrictive language or label requirements since those of skill in the art are well versed in related X-Ray imaging apparatuses, computer and operational controls and technologies of radiographic devices and all their sub components, including various circuits and combinations of circuits and modules and elements without departing from the scope and spirit of the present invention.

Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

The inventor sets forth illustrative Embodiments of the present invention based on the following FIGs. FIG. 1A-FIG. 1C are schematic views of the X-ray imaging apparatus according to the aspect of the present invention. FIG. 2 is a block diagram illustrating the main control system of the X-ray imaging apparatus according to the aspect of the present invention.

The X-ray imaging apparatus (system) according to one alternative aspect of the present invention further includes a console 1 and a high-voltage device 2 that are installed in an operation room 101, in which an operator implements the X-ray imaging operation; and a lying table 3, a wall-stand 5 and an imaging unit 4 that are installed in the imaging room 100. The imaging room 100 and the operation room 101 are separated and blocked from each other by the partition-wall 102.

The console 1 installed in the operation room 101 includes a display unit 11 formed by a liquid crystal display and so forth, and an operation unit 12 having a keyboard and a mouse and so forth used to execute a variety of operations. The display unit 11 displays an X-ray image. In addition, the console 1 includes a flat panel detector identification unit 14 and an exposure sensitivity memory unit 15. set forth later. Referring to FIG. 2, the control unit 13 controls the console 1. The console 1 is connected to an in-hospital local network 103 that is an in-house communication relative to the in-hospital subject management system. Relative to the console 1, the imaging region and the imaging method are selected applying the operation unit 12, so that either the lying table 3 or the wall stand 5 can be selected for use. The operation unit 12 of the console 1 functions as an operation method selection unit according to the aspect of the present invention to execute such selection.

Figure 3:
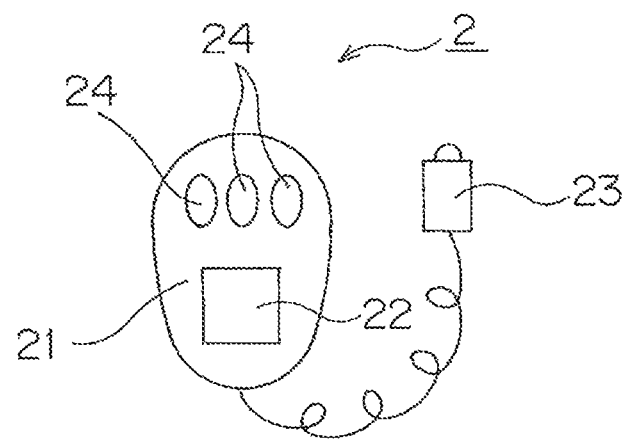
FIG. 3 illustrates a schematic view of a high-voltage device 2.

FIG. 3 is illustrating a schematic view of a high-voltage device 2.

The high-voltage unit 2 is installed to the partition-wall 102 in the operation room 101. The high-voltage unit 2 comprises: the display unit 22 having a touch panel type liquid crystal display; the operation panel 21 having an input key (button) 24; a switch 23 that directs to start an X-ray irradiation from the X-ray tube 42; an exposure control unit 28 (referring to FIG. 2) that suspends the X-ray irradiation based on the integrated value of the X-ray dose detected by an X-ray dose sensor 36 set forth later. The high-voltage unit 2 sets up a tube voltage of the X-ray tube 42 and a tube electric current, set forth later, or an X-ray irradiation condition including such as an X-ray irradiation time length and so forth. Referring to FIG. 2, the control unit 25 controls the high-voltage unit 2.

Repeatedly, referring to FIG. 1A-FIG. 1C, FIG. 2, the lying table 3 comprises: a tabletop 31 on which the subject lies; a holding unit 39 mounting the flat panel detector (FPD) 33A, as an X-ray detector, inside thereof; a lifting unit 34 that shifts up-and-down the holding unit 39 and the tabletop 31; and the X-ray dose sensor 36. The control unit 38 controls the lying table 3. In addition, other than the flat panel detector 33A, the other kind flat panel detector 33B and flat panel detector 33C may be used. Such multiple kinds of flat panel detectors 33A, 33B, 33C are used selectively. Such flat panel detectors 33A, 33B, 33C in the specification and FIGs of the present invention may be called collectively "flat panel detectors 33".

The X-ray dose sensor 36 installed to the lying table 3 is also called a radiation dose detector and used to obtain constantly a concentration of an adequate X-ray image. The X-ray dose sensor 36 comprises; a fluorescent screen that generally converts an X-ray to light; and a photo sensor that detects the light emitted from the fluorescent screen; and has a function to convert the X-ray dose per time unit to an electric signal. The electric signal indicating the X-ray dose is sent out to the exposure control unit 28 of the high-voltage unit 2. The exposure control unit 28 suspends the X-ray irradiation from the X-ray tube 42 based on an integrated value of the X-ray dose detected by the X-ray dose sensor 36. In addition, such aspect may be called a photo timer.

The wall-stand 5 comprises: a pedestal 53; a wall 51 in front of which a subject stands; a holding unit 59 on which the flat panel detector 33 is mountable; a lifting unit 52 that shifts the holding unit 50 up-and-down; and an X-ray dose sensor 56 having the same structure and function as the X-ray dose sensor 36 set forth above. The control unit 54 controls the wall-stand 5.

An imaging unit 4 comprises: a base 61 movable in the orthogonal direction relative (parallel) to the ceiling of the imaging room 100; a support column 62 extending downward from the base 61; a shifting unit 63 telescopic and rotatable relative to the support column 62; and a supporting axis (not shown in FIG.), mounted on the bottom of the shifting unit 63, that rotates an operation unit 41, the X-ray tube 42, and a collimator 43 as a unit, around the horizontal axis. Accordingly, the operation unit 41, the X-ray tube 42, and the collimator 43 are movable (shiftable) as a unit. Referring to FIG. 2, the control unit 48 controls the imaging unit 4.

The flat panel detector identification unit 14 set forth above identifies any of flat panel detectors 33A, 33B, 33C which are being used for the X-ray imaging. At this time, for example, the flat panel detector identification unit 14 identifies the flat panel detectors being used for the X-ray imaging by inputting the kind of flat panel detectors 33A, 33B, 33C being used for X-ray imaging by utilizing the operation unit 12 of the console 1. At this time, such identification of any of flat panel detectors 33A, 33B, 33C that is being used for the X-ray imaging can be implemented by reading out an identifier sign such a bar-cord and so forth attached to multiple kinds of flat panel detectors 33A, 33B, 33C. In addition, an identifier that identifies the kind of flat panel detectors 33 is attached to the holding units 39, 59 holding the flat panel detectors 33, and when the flat panel detectors 33 are mounted on the holding units 39, 59, the respective holding units 39, 59 can identify which flat panel detector among the flat panel detectors 33A, 33B, 33C is held.

At this time, relative to the X-ray imaging apparatus according to the aspect of the Embodiment, when the holding unit 39 of the lying table 3 or the holding unit 59 of the wall stand 5 holds the flat panel detectors 33, it is preferable that the flat panel detectors 33 held by each holding unit 39, 59, is assigned to any of flat panel detectors 33A, 33B, 33C by a variety of methods set forth above, and then each holding units 39, 59 are selected, so that the kind of the flat panel detectors 33 is identified. In addition, in such case, it is preferable that reading the imaging condition using such as anatomical program and so forth when X-ray imaging starts is executed, and identification of the flat panel detectors 33 being used is executed when either the lying table 3 or the wall-stand 5 is selected.

As discussed above, "identification of the flat panel detectors 33" is a specific action including the aspect in which the flat panel detectors 33 used for the X-ray imaging are identified.

In addition, the exposure sensitivity memory unit 15 of the console 1 stores the sensitivities of multiple flat panel detectors 33A, 33B, 33C used for the X-ray imaging. Further specifically, the exposure sensitivity memory unit stores an exposure sensitivity indicating the relationship between the integrated values of the X-ray detected by the X-ray dose sensor 36 and the time when the X-ray irradiation from the X-ray tube 42 is subject to suspension while corresponding to the respective flat panel detectors 33A, 33B, 33C. At this time, according to the aspect of the present Embodiment, three kinds of exposure sensitivities are stored as for each flat panel detectors 33A, 33B, 33C because the flat panel detectors used for the X-ray imaging are three kinds of 33A, 33B, 33C.

On the other hand, when a further large number of flat panel detectors is used, such flat panel detectors are classed in multiple kinds, so that multiple exposure sensitivities can be stored corresponding to flat panel detectors classed in multiple kinds. For example, when 10 kinds of flat panel detectors are used for the X-ray imaging and when such kinds of flat panel detectors are classed in 3 kinds every sensitivity thereof, three kinds of exposure sensitivities should be stores.

When suspends the X-ray irradiation from the X-ray tube 42 based on the integrated value of X-ray dose detected by the X-ray dose sensor 36, an exposure control unit 28 of the high-voltage unit 2 set forth above selects one of three kinds of exposure sensitivities stored in the exposure sensitivity memory unit 15 and determines the time when the X-ray irradiation suspends based on the selected exposure sensitivity following the information that indicates the flat panel detectors 33, which is identified by the flat panel detector identification unit 14, is used for the X-ray imaging is any of flat panel detectors 33A, 33B, 33C.

Figure 4:
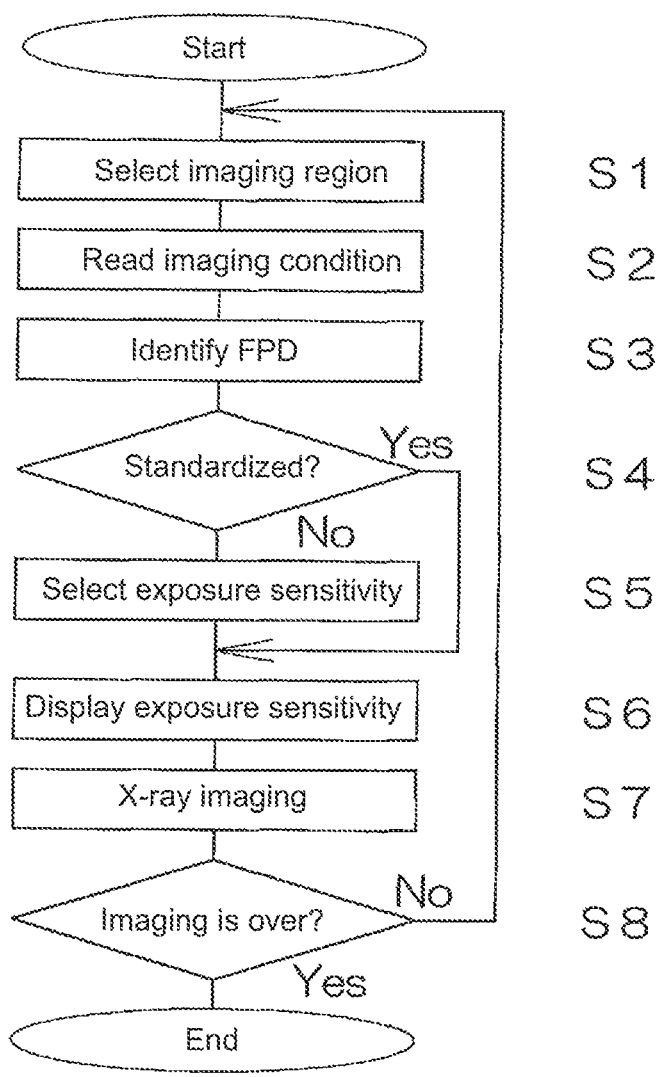
FIG. 4 is a flow-chart illustrating an X-ray imaging operation relative to the X-ray imaging apparatus according to the aspect of the present invention.

Next, the inventor set forth an X-ray imaging operation with X-ray imaging apparatus having the above structure. FIG. 4 is a flow-chart illustrating the X-ray imaging operation using the X-ray imaging apparatus according to the aspect of the present invention.

When an X-ray imaging starts, first, the console 1 selects the imaging region (Step S1). Accordingly, the data relative to the subject 20 is forwarded from the in-hospital local area network 103 and reading of the imaging condition using the anatomical program and so forth is executed (Step S2).

Figure 5A:
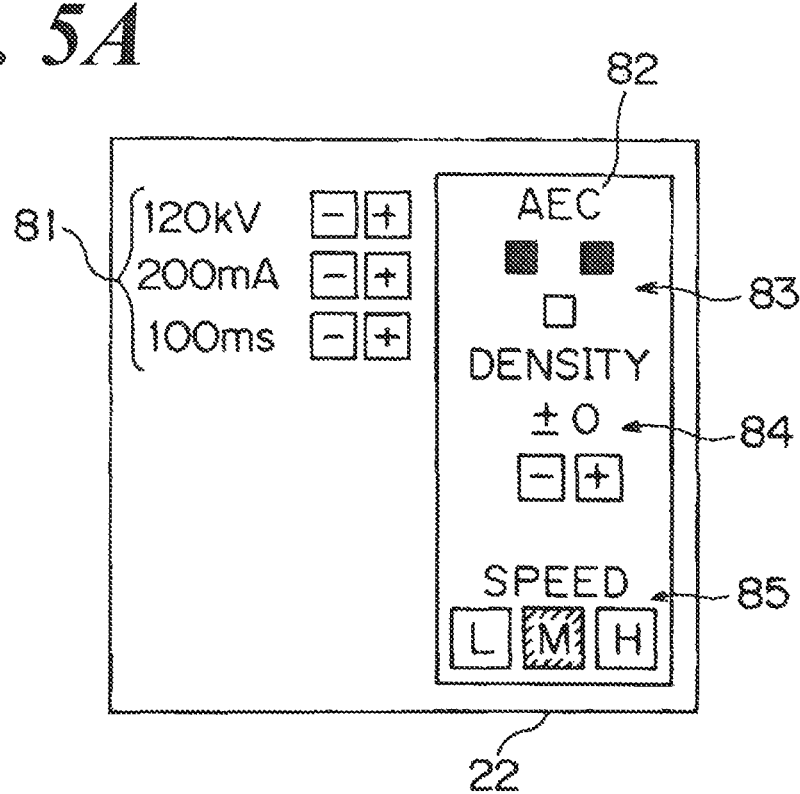
FIG. 5A, 5B are schematic views illustrating images displayed on the display unit 22 of the operation panel 21 of the high-voltage device 2.
Figure 5B:
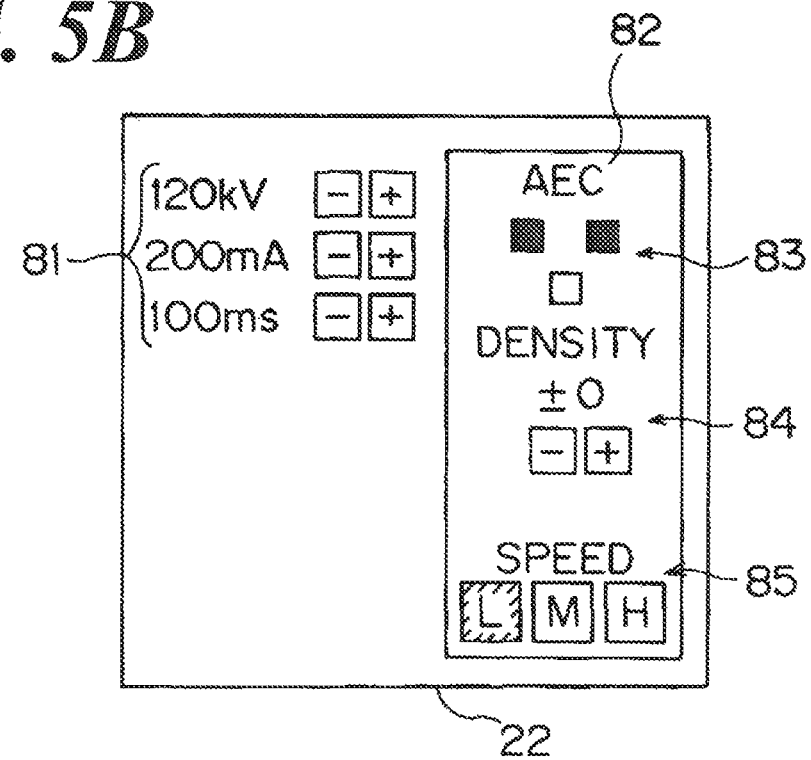

FIG. 5A, 5B are schematic views illustrating images displayed on the display unit 22 of the operation panel 21 of the high-voltage device 2.

Referring to FIG. 5A, the tube voltage (120 KV), the tube electric current (200 mA) and the time length of X-ray irradiation (100 ms) read as the imaging conditions are displayed in the imaging condition display region 81 of the display unit 22 of the operation panel 21 of the high-voltage unit 2. In addition, the AEC display region 82 relative to the display unit 22 includes a use region display 83, in which the region is used for AEC of the X-ray dose sensor 36, relative to a finely adjusted concentration display 84, and an exposure sensitivity display 85. Referring to FIG. 5A, the middle-sensitivity M is selected as an exposure sensitivity, so that the light of the display region for the middle-sensitivity M is turned on to indicate the state therefor.

Next, the flat panel detectors 33 used for the X-ray imaging are identified (Step S3). At this time, for example, any of the holding unit 39 of the lying table 3 and the holding unit 59 of the wall-stand 5 is identified to be used based on the reading imaging condition, so that the flat panel detectors 33, which are held thereby and used for the X-ray imaging, are automatically identified. In addition, the flat panel detector identification unit 14 may identify the flat panel detectors being used for the X-ray imaging by inputting the data of the flat panel detectors 33A, 33B, 33C being used for X-ray imaging by utilizing the operation unit 12 of the console 1.

And, when the flat panel detectors 33 identified by the flat panel detector identification unit 14 are standardized settings (Step S4), the X-ray imaging is executed as-is (Step S7). At this time, the current-selected exposure sensitivity among the multiple exposure sensitivities stored in the exposure sensitivity memory unit 15 (the middle-sensitivity according to the aspect of the present Embodiment) is utilized to control the exposure. Specifically, the exposure control unit 28 of the high-voltage unit 2 suspends the X-ray irradiation from the X-ray tube 42 when an integrated value of the X-ray doses detected by the X-ray dose sensor 36 reaches to the setting-value set at the middle-sensitivity M. This time, the X-ray irradiation time length is shorter than the irradiation time duration 100 ms read in advance.

On the other hand, when the flat panel detectors 33 identified by the flat panel detector identification unit 14 are not a standardized setting (Step S4), an exposure sensitivity (either low-sensitivity L or high-sensitivity H) corresponding to the flat panel detectors 33 used for the X-ray imaging is selected from multiple exposure sensitivities stored in the exposure sensitivity memory unit 15 of the console 1 (Step S5).

Then, the selected exposure sensitivity is displayed on the display unit 22 of the operation panel 21 of the high-voltage device 2. FIG. 5B is illustrating the case when the low-sensitivity L is selected as an exposure sensitivity. At this time, the light of the display region of the low-sensitivity L turns on to indicate the selected low-sensitivity L as the exposure sensitivity. When the high-sensitivity H is selected as an exposure sensitivity, the light of the display region of the high-sensitivity H turns on. In such way, the selected exposure sensitivity is displayed, so that the operator can easily recognize the relationship between the selected flat panel detectors 33 and the required exposure sensitivity at that time as well as using the conventional intensifying screen.

And then after, an X-ray imaging is executed (Step S7). At this time, the current-selected exposure low-sensitivity L among the multiple exposure sensitivities stored in the exposure sensitivity memory unit 15 is utilized to control the exposure. Specifically, the exposure control unit 28 of the high-voltage unit 2 suspends the X-ray irradiation from the X-ray tube 42 when an integrated value of the X-ray doses detected by the X-ray dose sensor 36 reaches to the setting-value set at the low-sensitivity L.

Subsequently, the above steps are repeated until an entire X-ray imaging is completed (Step S8).

In addition, according to the aspect of the present Embodiment set forth above, for convenience of explanation, the case in which three kinds flat panel detectors 33A, 33B, 33C for an X-ray imaging are used is set forth, but in fact, a further large number of flat panel detectors 33 is used. Even in such event, such large number of flat panel detectors 33 are classed into any exposure sensitivity of the low-sensitivity L, the middle-sensitivity M and the high-sensitivity H and the X-ray imaging is implemented by the same steps as the steps set forth above. At this time, the exposure sensitivity can be classed to two kinds or more than 4 kinds.

REFERENCE OF SIGNS

1 Console
2 High-voltage unit
3 Table
4 Imaging unit
5 Stand unit
11 Display unit
12 Operation unit
13 Control unit
14 Flat panel detector (FPD) identification unit
15 Exposure sensitivity memory unit
20 Subject
21 Operation panel
22 Display unit
31 Tabletop
33 Flat panel detector
36 X-ray dose sensor
39 Holding member
42 X-ray tube
56 X-ray dose sensor
59 Holding member
82 AEC display region
100 Imaging table
101 Operation unit
102 Screen
103 In-hospital local network Those of skill would further appreciate that the various illustrative logical blocks, modules, circuits, method steps or algorithm steps described in connection with the embodiments disclosed herein may be implemented as electronic hardware, computer software running on a specific purpose machine that is programmed to carry out the operations described in this application, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments.

The various illustrative logical blocks, modules, and circuits described in connection with the embodiments disclosed herein, may be implemented or performed with a general or specific purpose processor, or with hardware that carries out these functions, e.g., a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. The processor can be part of a computer system that also has an internal bus connecting to cards or other hardware, running based on a system BIOS or equivalent that contains startup and boot software, system memory which provides temporary storage for an operating system, drivers for the hardware and for application programs, disk interface which provides an interface between internal storage device(s) and the other hardware, an external peripheral controller which interfaces to external devices such as a backup storage device, and a network that connects to a hard wired network cable such as Ethernet or may be a wireless connection such as a RF link running under a wireless protocol such as 802.11. Likewise, an external bus may be any of but not limited to hard wired external busses such as IEEE-1394 or USB. The computer system can also have a user interface port that communicates with a user interface, and which receives commands entered by a user, and a video output that produces its output via any kind of video output format, e.g., VGA, DVI, HDMI, display port, or any other form. This may include laptop or desktop computers, and may also include portable computers, including cell phones, tablets such as the IPAD™ and Android™ platforms, and all other kinds of computers and computing platforms.

A processor may also be implemented as a combination of computing devices, e.g., a combination of a DSP and a microprocessor, a plurality of microprocessors, one or more microprocessors in conjunction with a DSP core, or any other such configuration. These devices may also be used to select values for devices as described herein.

The steps of a method or algorithm described in connection with the embodiments disclosed herein may be embodied directly in hardware, in a software module executed by a processor, using cloud computing, or in combinations. A software module or programs or algorithms may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of tangible storage medium that stores tangible, non-transitory computer based instructions. An exemplary storage medium is coupled to the processor such that the processor can read information from, and write information to, the storage medium. In the alternative, the storage medium may be integral to the processor. The processor and the storage medium may reside in reconfigurable logic of any type.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer.

The computers described herein may be any kind of computer, either general purpose, or some specific purpose computer such as a workstation. The programs may be written in C, or Java, Brew or any other programming language. The programs may be resident on a storage medium, e.g., magnetic or optical, e.g. the computer hard drive, a removable disk or media such as a memory stick or SD media, or other removable medium. The programs may also be run over a network, for example, with a server or other machine sending signals to the local machine, which allows the local machine to carry out the operations described herein.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. An X-ray imaging apparatus, comprising:
    an X-ray tube;
    one or more X-ray detectors that detects an X-ray irradiated from said X-ray tube to a subject and transmitted through said subject;
    an X-ray dose sensor that detects an X-ray dose that is irradiated from said X-ray tube and transmits through said subject;
    an exposure control unit that suspends the X-ray irradiation from said X-ray tube based on an integrated value of the X-ray dose detected by said X-ray dose sensor;
    an exposure sensitivity memory unit that stores multiple exposure sensitivities that indicate a threshold value related to the integrated value of the X-ray dose while corresponding to a type and a class of said X-ray detector;
    an identification unit that automatically identifies an X-ray detector used for an X-ray imaging;

a selection unit that selects said exposure sensitivities, corresponding to the type and class of the X-ray detector identified by said identification unit, from said exposure sensitivity unit;

a comparison unit, in said exposure control unit, outputs a signal of a comparison result while comparing said exposure sensitivity selected by said selection unit and said integrated value of the X-ray dose detected said X-ray dose sensor; and said exposure control unit suspends the X-ray irradiation from said X-ray tube when said signal, which said comparison unit outputs, indicates that said integrated value of the X-ray dose detected by said X-ray dose sensor has reached to said exposure sensitivity selected by said selection unit.

2. The X-ray imaging apparatus, according to claim 1, wherein:

said at least one holding unit attachably and detachably holds multiple kinds of said X-ray detectors; and wherein said identification unit identifies the type and the class of the X-ray detector held by said holding unit.

3. The X-ray imaging apparatus, according to claim 1, further comprising:

a plurality of said at least one holding unit that hold said X-ray detectors; and an operation method selection unit that selects said holding unit; and wherein said identification unit identifies the type and class of said X-ray detector held by said holding unit selected by said operation method selection unit.

\* \* \* \* \*